(12) United States Patent
Domingo Pedral et al.

(10) Patent No.: US 8,202,906 B2
(45) Date of Patent: Jun. 19, 2012

(54) USE OF DOCOSAHEXANOIC ACID AS ACTIVE SUBSTANCE FOR THE TREATMENT OF LIPODYSTROPHY

(75) Inventors: Juan Carlos Domingo Pedral, Barcelona (ES); Pere Domingo Pedral, Barcelona (ES)

(73) Assignee: Proyecto Empresarial Brudy, S.L., Barcelona (ES)

( * ) Notice: Subject to any disclaimer, the term of this patent is extended or adjusted under 35 U.S.C. 154(b) by 826 days.

(21) Appl. No.: 10/535,220

(22) PCT Filed: Dec. 1, 2003

(86) PCT No.: PCT/IB03/05673
§ 371 (c)(1),
(2), (4) Date: May 17, 2005

(87) PCT Pub. No.: WO2004/050077
PCT Pub. Date: Jun. 17, 2004

(65) Prior Publication Data
US 2006/0178436 A1 Aug. 10, 2006

(30) Foreign Application Priority Data
Dec. 5, 2002 (ES) .................................. 200202963

(51) Int. Cl.
*A61K 31/20* (2006.01)
(52) U.S. Cl. ...................................................... 514/560
(58) Field of Classification Search .................... 514/560
See application file for complete search history.

(56) References Cited

U.S. PATENT DOCUMENTS
2004/0106591 A1* 6/2004 Pacioretty et al. ............ 514/184

FOREIGN PATENT DOCUMENTS
| DE | 4017979 | 12/1991 |
| EP | 0378824 | 7/1990 |
| FR | 2749133 | 12/1997 |

OTHER PUBLICATIONS

Connor WE, DeFrancesco CA, and Connor SL, "N-3 fatty acids from fish oil. Effects on plasma lipoproteins and hypertriglyceridemic patients," Annals of the New York Academy of Sciences, Jun. 1993, 683, 16-34.*
Holstein A, Plaschke A, and Egberts EH, "Lipodystrophy and metabolic disorders as complication of antiretroviral therapy of HIV infection," Experimental and Clinical Endocrinology and Diabetes, 2001, 109(8), 389-392.*
Jedwards International, Inc., http://www.bulknaturaloils.com/fishoil/epadha/tunaoil.html, accessed Jun. 28, 2010.*
Stedman's Medical Dictionary, 27th ed., Lippincott, Eilliams & Wilkins, Baltimore, 2000.*
Bégin, M.E. "Plasma Fatty Acid Levels in Patients with Acquired Immune Deficiency Syndrome and in Controls". Prostaglandins Leukotrienes and Essential Fatty Acids, vol. 37, No. 2,—Aug. 1989 pp. 135-137.
Esteban Martinez et al.; "Effects of Metformin or Gemfibrozil on the Lipodystrophy of HIV-Infected Patients Receiving Protease Inhibitors"; 2003 International Medical Press 1359-6535/02; pp. 403-410.
Patrick W.G. Mallon et al.; "Effect of Pravastatin on Body Composition and Markers of Cardiovascular Disease in HIV-Infected Men—A Randomized, Placebo-Controlled Study"; AIDS 2006, vol. 20, No. 7; pp. 1003-1010.
Derek C. Macallan et al.; "Treatment of Altered Body Composition in HIV-Associated Lipodystrophy: Comparison of Rosiglitazone, Pravastatin, and Recombinant Human Growth Hormone"; HIV Clinical Trials Jul.-Aug. 2008;9(4); pp. 254-268.
A. Calmy et al.; "No Significant Effect of Uridine or Pravastatin Treatment for HIV Lipoatrophy in Men Who Have Ceased Thymidine Analogue Nucleoside Reverse Transcriptase Inhibitor Therapy: A Randomized Trial*"; 2010 British HIV Association, HIV Medicine (2010), 11, pp. 493-501.

* cited by examiner

*Primary Examiner* — Paul Zarek
(74) *Attorney, Agent, or Firm* — Cozen O'Connor

(57) ABSTRACT

Use of an extract of animal, plant or microorganism-produced origin comprising docosahexaenoic acid as active substance for the manufacture of a medicament for the treatment of lipodystrophy in a mammal. The medicament is administered to a patient who is concomitantly receiving a highly active anti-retroviral therapy (HAART). The treatment is effective and overcomes the disadvantages of current lipodystrophy treatments in HIV-infected patients.

12 Claims, No Drawings

USE OF DOCOSAHEXANOIC ACID AS ACTIVE SUBSTANCE FOR THE TREATMENT OF LIPODYSTROPHY

FIELD OF THE INVENTION

This invention relates to the use of an extract of animal, plant or microorganism-produced origin comprising docosahexaenoic acid as active substance for the manufacture of a medicament for the treatment of lipodystrophy, particularly in patients infected by the HIV virus.

BACKGROUND OF THE INVENTION

Treatments have been available since the end of 1996 which are capable of controlling multiplication of the human immunodeficiency virus (HIV), which is the cause of acquired immune deficiency syndrome (AIDS). These treatments have been generically so-called highly active antiretroviral therapy (HAART). The current HAART characteristically consists in the combination of at least three drugs.

There are at present two families of antiretrovirals that inhibit key enzymes for viral replication and which are the reverse transcriptase inhibitors (nucleoside analogues, nucleotide analogues and nucleoside non-analogues) and the viral protease inhibitors.

However, such treatments are not capable of leading to eradication of the virus (elimination thereof) and, to keep the infection controlled they, therefore, have to be administered indefinitely, probably throughout the patient's entire lifetime.

Such treatments, of undoubted efficacy in controlling viral replication, are nevertheless not innocuous for patients, and because the exposure time thereto is, necessarily, very lengthy, their toxic effects tend to accumulate over time.

Since 1997 there began to be detected patients submitted to HAART who presented disorders not previously described in body-fat distribution, accompanied by plasma lipid level disorders.

Briefly, the patients show loss of fat in the face, buttocks, extremities and thorax, accompanied by accumulation of fat inside the abdomen, the back of the neck and in the breast area in women, together with increase plasmatic levels of cholesterol, triglycerides, lowering of HDL cholesterol (protective cholesterol) and increase of LDL cholesterol (harmful cholesterol), insulin resistance (occasionally diabetes) and occasionally arterial hypertension.

This entire set of situations is known as lipodystrophy syndrome.

Approaches to the treatment of lipodystrophy can be summed up in five broad groups:

(a) Strategies which modify the HAART components, so that this cannot be suppressed without running the risk of losing control over viral replication.

(b) Drugs (e.g. methformine, rosiglytazone) which cause sensitisation to the action of insulin.

(c) Drugs which aim to control the lipidic aspects of the syndrome, such as fibrates and statines, which can improve (though rarely normalise) plasmatic lipid disorders.

(d) Hormone treatments (e.g. growth hormones).

(e) Facial cosmetic surgery with implants to correct fat loss.

None of the treatments tested so far have shown any efficacy in reversing the disorders in body fat distribution, and the control of lipidic disorders using such measures has been incomplete.

It should be mentioned that the foregoing tested pharmacological treatments are not without toxic effects on the patient, which can, occasionally, be serious. They furthermore, mean an additional drug burden, and some of them interact in a potentially serious way with the antiretroviral drugs which HIV-infected patients cannot stop taking.

There is still, therefore, no available treatment for lipodystrophy, in particular in HIV-infected patients, which is effective and does not give rise to the disadvantages of the treatments currently known.

DESCRIPTION OF THE INVENTION

The inventors of the present invention have found a treatment effective against lipodystrophy and which, furthermore, overcomes the disadvantages presented by the current treatments for said illness in HIV-infected patients.

This invention relates to the use of an extract of animal, plant or microorganism-produced origin that comprises docosahexaenoic acid as active substance for the manufacture of a medicament for the treatment of lipodystrophy in a mammal.

Docosahexaenoic acid (DHA) is an omega-3 fatty acid which contains 22 atoms of carbon, being six of them unsaturated (C22:6 n-3). Such acid is found, mainly, in fish (for example, tuna), microorganisms and plants.

In this invention, "extract of animal, plant or microorganism-produced origin that comprises docosahexaenoic acid as active substance" is taken to mean a composition which includes docosahexaenoic acid, which is obtained from fish, microorganisms and plants, by means of extraction, and optionally, chemical-modification procedures known to those skilled in the art.

In this invention, "microorganism" is taken to mean any microscopic organism, including but not limited to bacteria, protozoa, fungi, viruses and algae, and any of their variants produced by genetic engineering, which are characterized in that they produce DHA.

Docosahexaenoic acid can, thus, be one occurring naturally or one modified chemically. The chemical forms in which the DHA can be found therefore include, but are not restricted to, the free acid of DHA, DHA esters with natural or synthetic alcohols and lipidic forms such as the glycerides, phospholipids, sphingolipids and gangliosides.

In particular, this invention relates to the use of an extract of animal, plant or microorganism-produced origin that comprises docosahexaenoic acid as active substance for the manufacture of a medicament for the treatment of lipodystrophy in mammals, said extract having a DHA content that ranges between 5% and 100% (w/w), preferably between 50% and 100% (w/w).

Surprisingly, the inventors of the present invention have found that the fact that the DHA is a physiological substance possessing multiple actions on the adipocytes (fat cells) and on plasma lipid levels permits the effective treatment of lipodystrophy.

Principal among these is its ability to promote differentiation (multiplication) of the adipocytes, reduce blood triglyceride and cholesterol levels, increase HDL cholesterol level, reduce LDL cholesterol level, and reduce arterial blood pressure.

Additionally, the DHA possesses anti-inflammatory properties (it inhibits the secretion of alpha tumour necrosis factor) which, as will be shown below, is high in patients with lipodystrophy.

In a second aspect, a dosage of the medicament of the invention is administered equal to or higher than 100 mg/day, a dosage of 4 grams per day being preferable.

A medicament according to this invention can be administered orally or parenterally.

Depending on the chosen route of administration, pharmaceutically acceptable diluents, excipients and/or carriers of the active substance can be included, such as liposomes, microemulsions, micelles, etc.

In a third aspect, the medicament of the invention is administered to a human, preferably an HIV-infected human.

It has been found, indeed, that administration of the medicament of the invention in cultured adipocytes is capable of inhibiting the toxic effects caused by the exposure of these cells to the antiretroviral drugs.

Therefore, and taking into account the beneficial effects pointed out above, the medicament of this invention can perform a beneficial action on lipodystrophy syndrome, especially in HIV-infected patients treated under HAART regimens, having the following advantageous aspects in relation to current treatments:
1. adipocytary differentiation promoter activity;
2. hypolipemiant activity;
3. anti-inflammatory activity (reduction of the alpha tumour necrosis factor);
4. antihypertensive activity;
5. absence of side effects at the dosages administered;
6. absence of interactions with the antiretroviral regimen components due to it being a medicament that is not metabolised by routes common to those of the antiretroviral drugs (it should be remembered that the patient cannot dispense with HAART).

There follows, by way of non-restrictive illustration, an example of embodiment of this invention.

EXAMPLES

Example 1

Four HIV-infected patients under HAART regimen and presenting lipodystrophy syndrome were administered 4 grams/day of a tuna oil with a DHA content of 70%. After three months' administration of DHA to said patients, the following discoveries were made, even taking account of the short period of administration:
1. Partial reversal of body-fat distribution disorders, with
  1.1 improvement in facial fat loss;
  1.2 improvement in fat loss in buttocks and extremities;
  1.3 no increase in intra-abdominal fat.
2. Mean reduction of 56% in the plasma triglycerides number.
3. Mean reduction of 25% in the total plasma cholesterol number.
4. Mean increase of 9% in the plasma HDL cholesterol number.
5. Mean reduction of 18% in the plasma LDL cholesterol number.

These results, shown in the table on the following page, allow us to conclude that the administration of DHA at dosages of 4 grams a day over the course of 3 months is capable of improving lipodystrophy and the lipidic disorders associated with it.

TABLE

| | before the treatment | | | | | after 3 months of treatment | | | | |
|---|---|---|---|---|---|---|---|---|---|---|
| | VLDL | COL. | TG | HDL | LDL | VLDL | COL. | TG | HDL | LDL |
| Patient 1 | 1.27 | 6.8 | 7.1 | 1.1 | 3.67 | 0.46 | 5.46 | 1 | 1.57 | 3.43 |
| Patient 2 | 3.96 | 9.95 | 8.62 | 1.12 | 4.87 | 3.74 | 9.48 | 10.66 | 0.91 | 3.35 |
| Patient 3 | 2.18 | 5.18 | 6.29 | 1.09 | 1.91 | 0.8 | 3.82 | 1.73 | 1.05 | 1.97 |
| Patient 4 | 11.41 | 19.13 | 30.8 | 1.92 | 0.79 | 1.82 | 9.9 | 3.41 | 0.98 | 6.67 |

Example 2

From the four patients treated with DHA at elevated dosages (1.5 g/day), all of them have been monitored for 300 days and, although notable fluctuations are observed, especially regarding to the triglicerids (see Table 2), after 300 days of monitoring, the reduction's mean in the number of triglycerids with respect to the basal level is 66% and for the cholesterol is 28.0%. At the same time, the HDL cholesterol shows a drop op 11.6%.

All patients have improved their fat redistribution, from the point of view subjective and according to the skill's criterion.

TABLE 2

| | before the treatment | | | | | 15 days of treatment | | | | | 30 days of treatment | | | | |
|---|---|---|---|---|---|---|---|---|---|---|---|---|---|---|---|
| Patient | COL. | TG | HDL | LDL | VLDL | COL. | TG | HDL | LDL | VLDL | COL. | TG | HDL | LDL | VLDL |
| 1 | 6.8 | 7 | 1.1 | 3.67 | 1.27 | 6.37 | 1.16 | 1.7 | 4.14 | 0.53 | 6.16 | 1.35 | 1.79 | 3.7 | 0.62 |
| 2 | 9.95 | 8.6 | 1.12 | 4.87 | 3.96 | 9.74 | 5.98 | 0.98 | 6.07 | 2.61 | 8.4 | 6.9 | 0.86 | 4.3 | 3.18 |
| 3 | 5.18 | 6.2 | 1.09 | 1.91 | 2.18 | 3.92 | 3.11 | 1.05 | 1.86 | 1.01 | 4.07 | 3.09 | 1.06 | 2.0 | 0.97 |
| 4 | 19.13 | 30 | 1.92 | 0.79 | 11.41 | 8.73 | 5.18 | 1.03 | 5.35 | 2.35 | 8.5 | 5.74 | 1.16 | 5.0 | 2.26 |

| | 60 days of treatment | | | | | 120 days of treatment | | | | | 180 days of treatment | | | | |
|---|---|---|---|---|---|---|---|---|---|---|---|---|---|---|---|
| Patient | COL. | TG | HDL | LDL | VLDL | COL. | TG | HDL | LDL | VLDL | COL. | TG | HDL | LDL | VLDL |
| 1 | 5.46 | 1 | 1.57 | 3.43 | 0.46 | 5.49 | 1.45 | 1.56 | 3.26 | 0.67 | 6.15 | 2.63 | 1.56 | 3.38 | 1.21 |
| 2 | 9.48 | 10.66 | 0.91 | 3.35 | 3.74 | 8.24 | 6.36 | 1.08 | 4.6 | 2.56 | 9.64 | 15.75 | 1.04 | 2.3 | 4.38 |

TABLE 2-continued

| | | | | | | | | | | | | | | | |
|---|---|---|---|---|---|---|---|---|---|---|---|---|---|---|---|
| 3 | 3.82 | 1.73 | 1.05 | 1.97 | 0.8 | 3.47 | 1.51 | 1.16 | 1.61 | 0.7 | 3.76 | 2.87 | 0.94 | 1.5 | 132 |
| 4 | 9.9 | 3.41 | 0.98 | 6.67 | 1.82 | 13.63 | 31.7 | 0.7 | 1.46 | 9.67 | 13.21 | 16.37 | 1.48 | 2.09 | 3.97 |

| | 240 days of treatment | | | | | 300 days of treatment | | | | |
|---|---|---|---|---|---|---|---|---|---|---|
| Patient | COL. | TG | HDL | LDL | VLDL | COL. | TG | HDL | LDL | VLDL |
| 1 | 5.7 | 1.59 | 1.67 | 3.3 | 0.73 | 6.01 | 1.57 | 1.23 | 4.06 | 0.72 |
| 2 | 8.1 | 5.36 | 0.98 | 4.93 | 2.12 | 9.3 | 7.21 | 1.08 | 5.31 | 2.92 |
| 3 | 4.04 | 1.85 | 1.09 | 2.1 | 0.85 | 4.34 | 1.62 | 0.89 | 2.7 | 0.75 |
| 4 | 5.33 | 2.18 | 1.17 | 3.16 | 1 | 4.27 | 1.36 | 1.22 | 2.42 | 0.63 |

The invention claimed is:

1. A method for treating a patient afflicted with lipodystrophy so as to increase the amount of fat in the patient's face, buttocks or extremities without causing an increase in the patient's intra-abdominal fat, consisting of administering a composition comprising an effective amount higher than or equal to 100 mg/day of a docosahexaenoic acid as the only active substance of animal, plant or microorganism-produced origin, wherein the patient is concomitantly receiving a highly active anti-retroviral therapy (HAART), thereby treating lipodystrophy in the patient.

2. The method of claim 1, wherein the effective amount of the docosahexaenoic acid is 4 grams/day.

3. The method of claim 1, where the administration of the docosahexaenoic acid promotes adipocytary differentiation.

4. The method of claim 1, wherein the docosahexaenoic acid reduces alpha tumour necrosis factor.

5. The method of claim 1, wherein the docosahexaenoic acid is capable of inhibiting the toxic effects caused by the administration of an antiretroviral drug.

6. The method of claim 1, wherein the docosahexaenoic acid is administered orally.

7. The method of claim 1, wherein the docosahexaenoic acid is administered parenterally.

8. The method of claim 1, wherein the patient is a human patient.

9. The method of claim 8, wherein the human patient is infected with the HIV virus.

10. The method of claim 1, wherein the patient is afflicted with facial fat loss.

11. The method of claim 1, wherein the patient is afflicted with fat loss in the buttocks and extremities.

12. The method of claim 1, wherein the patient is afflicted with an increase in intra-abdominal fat.

* * * * *